United States Patent
Wang et al.

(10) Patent No.: US 9,199,004 B2
(45) Date of Patent: *Dec. 1, 2015

(54) POLYMER-BIOCERAMIC COMPOSITE IMPLANTABLE MEDICAL DEVICE WITH DIFFERENT TYPES OF BIOCERAMIC PARTICLES

(71) Applicant: Abbott Cardiovascular Systems Inc., Santa Clara, CA (US)

(72) Inventors: Yunbing Wang, Sunnyvale, CA (US); David C. Gale, Kennesaw, GA (US); Syed F. A. Hossainy, Hayward, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 86 days.

This patent is subject to a terminal disclaimer.

(21) Appl. No.: 13/933,071

(22) Filed: Jul. 1, 2013

(65) Prior Publication Data

US 2014/0018907 A1 Jan. 16, 2014

Related U.S. Application Data

(63) Continuation of application No. 13/096,655, filed on Apr. 28, 2011, now abandoned, which is a continuation of application No. 11/823,931, filed on Jun. 29, 2007, now Pat. No. 7,955,381.

(51) Int. Cl.
*A61L 27/40* (2006.01)
*H03F 1/56* (2006.01)
*H03F 3/191* (2006.01)

(52) U.S. Cl.
CPC ............... *A61L 27/40* (2013.01); *H03F 1/565* (2013.01); *H03F 3/191* (2013.01)

(58) Field of Classification Search
CPC ..................................................... A61K 6/0273
USPC ............................................ 623/23.56, 23.73
See application file for complete search history.

(56) References Cited

U.S. PATENT DOCUMENTS

| | | | | |
|---|---|---|---|---|
| 5,077,132 A | * | 12/1991 | Maruno et al. | 428/426 |
| 5,626,861 A | * | 5/1997 | Laurencin et al. | 424/426 |
| 6,027,742 A | * | 2/2000 | Lee et al. | 424/422 |
| 6,117,456 A | * | 9/2000 | Lee et al. | 424/602 |
| 6,296,667 B1 | * | 10/2001 | Johnson et al. | 623/23.61 |
| 6,376,573 B1 | * | 4/2002 | White et al. | 523/115 |
| 7,754,272 B2 | * | 7/2010 | Rowan et al. | 427/2.1 |
| 7,879,109 B2 | * | 2/2011 | Borden et al. | 623/23.76 |
| 7,959,940 B2 | * | 6/2011 | Gale et al. | 424/423 |
| 8,029,554 B2 | * | 10/2011 | Holman et al. | 623/1.1 |
| 8,110,222 B2 | * | 2/2012 | Hutchens et al. | 424/489 |
| 8,178,013 B2 | * | 5/2012 | Kim | 264/40.5 |
| 8,889,178 B2 | * | 11/2014 | Bagga et al. | 424/443 |
| 9,034,356 B2 | * | 5/2015 | Shimp et al. | 424/423 |
| 9,084,844 B2 | * | 7/2015 | Vallittu | 1/1 |
| 2003/0049329 A1 | * | 3/2003 | Lee et al. | 424/602 |
| 2004/0158330 A1 | * | 8/2004 | Muller et al. | 623/23.57 |
| 2006/0085080 A1 | * | 4/2006 | Bechgaard et al. | 623/23.43 |
| 2011/0081396 A1 | * | 4/2011 | Denry | 424/423 |
| 2011/0202126 A1 | * | 8/2011 | Wang et al. | 623/1.46 |
| 2012/0290073 A1 | * | 11/2012 | Wang | 623/1.15 |
| 2013/0101673 A1 | * | 4/2013 | Borden | 424/492 |
| 2014/0128991 A1 | * | 5/2014 | Atanasoska et al. | 623/23.72 |
| 2014/0163664 A1 | * | 6/2014 | Goldsmith | 623/1.11 |
| 2014/0228967 A1 | * | 8/2014 | Wittchow | 623/23.7 |
| 2015/0175485 A1 | * | 6/2015 | Gottwik et al. | |

* cited by examiner

*Primary Examiner* — Thomas J Sweet
*Assistant Examiner* — Seema Mathew
(74) *Attorney, Agent, or Firm* — Squire Patton Boggs (US) LLP

(57) ABSTRACT

Implantable medical devices fabricated from polymer/bioceramic composites with different types of bioceramic particles are disclosed.

15 Claims, 4 Drawing Sheets

POLYMER-BIOCERAMIC COMPOSITE IMPLANTABLE MEDICAL DEVICE WITH DIFFERENT TYPES OF BIOCERAMIC PARTICLES

CROSS-REFERENCE TO RELATED APPLICATIONS

This application is a division of U.S. patent application Ser. No. 13/096,655 which is a continuation of U.S. patent application Ser. No. 11/823,931, filed Jun. 29, 2007, now U.S. Pat. No. 7,955,381, the entire disclosure of both applications is incorporated herein by reference.

BACKGROUND OF THE INVENTION

1. Field of the Invention

This invention relates to implantable medical devices and methods of fabricating implantable medical devices.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Potential problems with degradable polymers that may be suitable for use in stents include inadequate toughness and a degradation rate that is slower than is desirable for certain treatments.

SUMMARY OF THE INVENTION

Various embodiments of the present invention include a stent comprising structural elements fabricated at least in part from a bioceramic/polymer composite, the composite having a plurality of bioceramic particles dispersed within a biodegradable polymer, the plurality of bioceramic particles comprising at least two types of bioceramic particles, at least two types having a different effect on the degradation rate of the polymer.

Further embodiments of the present invention include a stent comprising structural elements fabricated from a bioceramic/polymer composite, the composite having a plurality of bioceramic particles dispersed within a biodegradable polymer, the plurality of bioceramic particles comprising acidic particles and basic particles, the acidic particles and basic particles having different particle size distributions.

Additional embodiments of the present invention include a stent comprising structural elements fabricated from a bioceramic/polymer composite, the composite having a plurality of bioceramic particles dispersed within a biodegradable polymer, the plurality of bioceramic particles comprising at least two types of particles, wherein the degradation of a selected type of particle is reduced or prevented during a selected time frame by encapsulating some or all of the selected type of particles with a bioabsorbable polymer.

DETAILED DESCRIPTION OF THE INVENTION

Figures 1A, 1B:
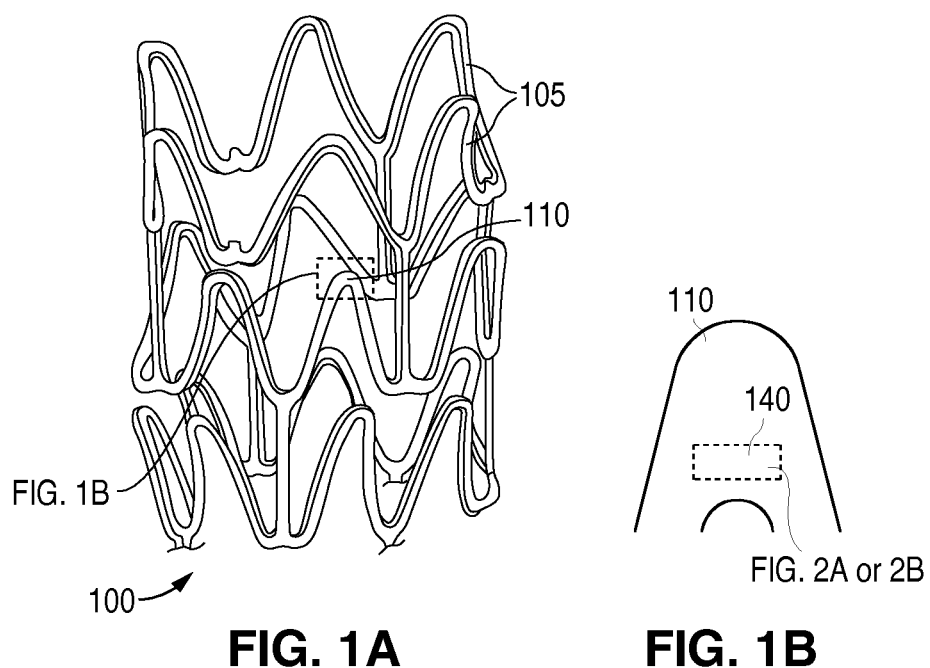
FIG. 1A depicts a three-dimensional view of a stent.
FIG. 1B depicts a section of a structural element from the stent depicted in FIG. 2A.

Certain embodiments of the present invention include an implantable medical device fabricated at least in part of a polymer/bioceramic composite including a matrix polymer and bioceramic particles dispersed within the polymer. Additional embodiments of the present invention include an implantable medical device fabricated at least in part of a polymer blend/bioceramic composite including a polymer blend and bioceramic particles dispersed within the blend. The polymer blend can have a continuous polymer phase and a discrete polymer phase within the continuous polymer phase. The bioceramic particles can be dispersed within the continuous phase, the discrete polymer phase, or both. The embodiments of the invention described herein are adapted to reduce or eliminate the shortcomings of biodegradable polymers with respect to use in implantable medical devices. Such shortcomings relate to degradation time, strength, and toughness.

As used herein, an "implantable medical device" includes, but is not limited to, self-expandable stents, balloon-expandable stents, stent-grafts, implantable cardiac pacemakers and defibrillators, leads and electrodes for the preceding, vascular grafts, grafts, artificial heart valves, and cerebrospinal fluid shunts.

An implantable medical device can be designed for the localized delivery of a therapeutic agent. A medicated implantable medical device may be constructed by coating the device or substrate with a coating material containing a therapeutic agent. The substrate of the device may also contain a therapeutic agent.

An implantable medical device can be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

An implantable medical device can have an ideal range of mechanical, chemical, or physical characteristics dictated by the requirements of its use in treatment. For example, mechanical characteristics include strength and toughness. Additionally, a biodegradable device can have an ideal range of degradation rate or time. A stent, for instance, requires adequate radial strength to support a lumen wall. A stent must also have sufficient toughness to resist cracking that can occur when the stent is crimped, expanded, or cycling loading upon deployment. Additionally, a stent also can have an ideal degradation time dictated by the length of a treatment. The embodiments described herein involve tuning the chemical properties of a polymer and incorporation of polymer and ceramic phases into the polymer to attain or approach ideal or desired degradation and mechanical properties of a device.

Some polymers that may be suitable for implantable medical devices such as stents have potential shortcomings. For example, some biodegradable polymers have a degradation rate that is slower than desired for certain stent treatments. As a result, the degradation time of a stent made from such polymers can be longer than desired. For example, a stent made from poly(L-lactide) (PLLA) can have a degradation time of between about two and three years. In some treatment situations, a degradation time of less than a year may be desirable, for example, between four and eight months.

Another shortcoming of some polymers is that their toughness is lower than desired, in particular, for use in stent applications. For example, polymers such as PLLA tend to be brittle under physiological conditions or conditions within a human body. Specifically, such polymers can have a Tg above human body temperature which is approximately 37° C. These polymers can exhibit a brittle fracture mechanism in which there is little or no plastic deformation prior to failure. As a result, a stent fabricated from such polymers can have insufficient toughness for the range of use of a stent.

Shortcomings of biodegradable polymer, such as poly(L-lactide), for an implantable medical device with respect to particular treatment applications of an implantable medical device can be addressed in at least two ways: (1) by modifying or altering the chemical composition of the polymer, (2) by including a particulate or dispersed ceramic phase within the polymer, and (3) by incorporating an additional polymeric phase within the matrix polymer. (1), (2), and (3) can be applied in alone or in combination.

With respect to (1), some embodiments can include incorporating functional groups in a polymer so that a resulting copolymer has an increased degradation rate. A device made from the resulting copolymer can thus have a decreased degradation time. In one embodiment, a copolymer or modified polymer can have a majority of a primary functional group, such as L-lactide, and at least one additional secondary functional group. The secondary functional group(s) can increase the degradation rate as compared to a polymer that is substantially or completely made up of the primary functional group. The increase in the degradation rate can be obtained by selecting a secondary functional group that has a greater hydrolytic activity and/or is more hydrophilic than the primary functional group. Additionally or alternatively, the increase can be due to a decrease in crystallinity of the modified polymer as compared to original polymer. The copolymers disclosed herein may be synthesized using techniques known to those of skill in the art. For example, it can be formed through the random copolymerization of LLA and GA monomers or LLA and dioxanone monomers.

In general, the degradation of a hydrolytically degradable polymer follows a sequence including water penetration into the polymer followed by hydrolysis of bonds in the polymer. Thus, the degradation of a polymer can be influenced by how fast functional groups undergo hydrolysis, the degree of hydrophilicity, and the diffusion rate of water through the polymer. Functional groups having a greater hydrolytic activity undergo hydrolysis at a faster rate. Such functional groups can be referred to as "hydrolysis-enhancing functional groups." For example, glycolide (GA) has a greater hydrolytic activity than L-lactide (LLA). Thus, a poly(L-lactide-co-glycolide) (LPLG) copolymer can have a higher degradation rate than PLLA. In addition, the diffusion rate of water through a polymer can be influenced by the degree of crystallinity since the diffusion rate of water through crystalline regions of a polymer is lower than amorphous regions. The larger percentage of amorphous regions allow greater water penetration and increase the degradation rate of the copolymer and decrease the degradation time of a stent made from the copolymer.

Additional embodiments of modifying a polymer can include incorporating functional groups in a polymer that increase the fracture toughness. Such a copolymer is more resistant to cracking than an unmodified polymer. A secondary functional group can be selected such that a homopolymer of the secondary functional group has a higher fracture toughness than the unmodified polymer. Such a functional group can be referred to as a "toughness-enhancing functional group." For example, functional groups that can increase the fracture toughness of a polymer include, but are not limited to, caprolactone (CL) and trimethylene carbonate (TMC). Dioxanone is both more hydrolytically active than PLLA and can enhance the fracture toughness of PLLA.

In one embodiment, a homopolymer of the second functional group is an elastomer. An "elastomer" or "rubbery" polymer refers to a polymer which can resist and recover from deformation produced by force, as in natural rubber. In one embodiment, elastomers or rubbery polymers can be stretched repeatedly to at least twice their original length and, immediately upon release of the stress, return with force to their approximate original length. In another embodiment, elastomers or rubbery polymers are substantially or completely amorphous polymers that are above their glass transition temperatures.

As the percentage of the secondary functional groups in the copolymer increase, the modulus of the copolymer can decrease as compared to the unmodified polymer. The decrease in modulus can be due to the decrease in crystallinity. This decrease in modulus is generally undesirable in stent applications since the modulus can reduce the ability of a stent to support a vessel. Thus, the weight percent of the secondary functional groups can be adjusted so that a stent can have adequate strength to act as structural support. However, a stent made from only a copolymer which has both adequate strength and a desired degradation time may not be possible with a copolymer having a specific combination of functional groups.

Generally, the strength, toughness, and the modulus of a polymer can be increased by including dispersed bioceramic particles within the polymer. Although the bioceramic particles increase the toughness, strength, and modulus, the increase in toughness may not be sufficient for some applications. Additionally, as the weight percent of bioceramic particles increases, the increase in strength and toughness does reach a limit.

In addition, fracture toughness of a low fracture toughness polymer under physiological conditions can be increased by blending it with another polymer having a higher or relatively high fracture toughness under physiological conditions. The higher fracture toughness polymer should also immiscible so that it forms a discrete polymer phase from the low fracture toughness polymer. The discrete phase can absorb energy arising from stress imparted to a device made from the blend to increase the fracture toughness of a device made from the blend. To ensure good energy transfer between interfaces of the phases, it is important that there be sufficient bonding or adhesion between the polymer phases. See, Y. Wang, etc. Journal of Polymer Science Part A: Polymer Chemistry, 39, 2001, 2755-2766.

As discussed above, various embodiments of the present invention include an implantable medical device fabricated at least in part from a polymer/bioceramic composite including a matrix polymer and bioceramic particles dispersed within the polymer. In these embodiments, the matrix polymer can be a copolymer.

One set of embodiments can include a composite in which the matrix polymer has a majority of one functional group and a minority of another functional group that has higher hydrolytic activity, such as glycolide. The increased hydrolytic activity and decreased crystallinity can increase the degradation rate of the matrix polymer.

Another set of embodiments can include a composite in which a matrix polymer has a functional group that enhances fracture toughness and increases the degradation rate of the matrix polymer. For example, the functional group can include caprolactone or trimethylene carbonate. The increase in the degradation rate can also be due to a decrease in crystallinity. Another set of embodiments can include a composite in which matrix polymer includes both a toughness-enhancing functional group and a hydrolysis-enhancing functional group.

Furthermore, the weight percents of the functional group(s) can be selected or adjusted to obtain a desired degradation rate of the polymer or degradation time of a stent made from the polymer. The weight percents of the functional groups can also be adjusted to obtain a desired fracture toughness. A desired degree of fracture toughness may correspond to a maximum number of cracks in a stent observed upon crimping or expansion.

It may be also be desirable to control the fracture toughness and/or the degradation rate of a structural element of a device made from a polymer/bioceramic composite by including an elastomeric block copolymer that forms a separate dispersed elastomeric phase within the matrix polymer. A further set of embodiments of an implantable medical device can include a structural element that is made at least in part of a polymer blend/bioceramic composite. In an embodiment, the polymer blend can include a mixture of a matrix polymer with a modifier polymer, the matrix polymer being a majority of the polymer blend. The modifier polymer can be a block copolymer with the matrix polymer being immiscible with at least some of the blocks or segments of the modifier polymer. The polymer blend/bioceramic composite can also include a plurality of bioceramic particles dispersed within the polymer blend.

Since at least some of the blocks or segments of the modifier polymer are immiscible with the matrix polymer, the composite has a continuous polymer phase and a dispersed or discrete polymer phase within the continuous polymer phase.

The bioceramic particles can be dispersed within the continuous phase, the discrete phase, or both the discrete and continuous phases.

Furthermore, the continuous phase can include the matrix polymer and the dispersed phase can include immiscible blocks of the modifier polymer. In one embodiment, the matrix polymer may have a relatively low fracture toughness at physiological conditions and the discrete polymer phase may be an elastomer with a relative higher fracture toughness at physiological conditions. For example, the matrix polymer can have a Tg above body temperature and the portion of the modifier polymer that forms the dispersed polymer phase can have a Tg below body temperature. The modifier polymer or dispersed phase tends to increase the toughness of the matrix polymer, and thus the composite. The use of a polymer blend as described may be most advantageous with a matrix polymer that includes hydrolysis-enhancing functional groups and few or none toughness-enhancing functional groups.

In some embodiments, the modifier polymer can have discrete phase segments and anchor segments. The discrete phase segments are immiscible with the matrix polymer so that the discrete phase segments are in the discrete phase. The anchor segments are miscible with the matrix polymer so that the anchor segments at least partially phase separate from the discrete phase into the continuous phase.

FIG. 1A depicts a three-dimensional view of a stent 100. In some embodiments, a stent may include a pattern or network of interconnecting structural elements 105. Stent 100 may be formed from a tube (not shown). The pattern of structural elements 110 can take on a variety of patterns. The structural pattern of the device can be of virtually any design. The embodiments disclosed herein are not limited to stents or to the stent pattern illustrated in FIG. 1A. The embodiments are easily applicable to other patterns and other devices. The variations in the structure of patterns are virtually unlimited. A stent such as stent 100 may be fabricated from a tube by forming a pattern with a technique such as laser cutting or chemical etching.

Figure 2A:
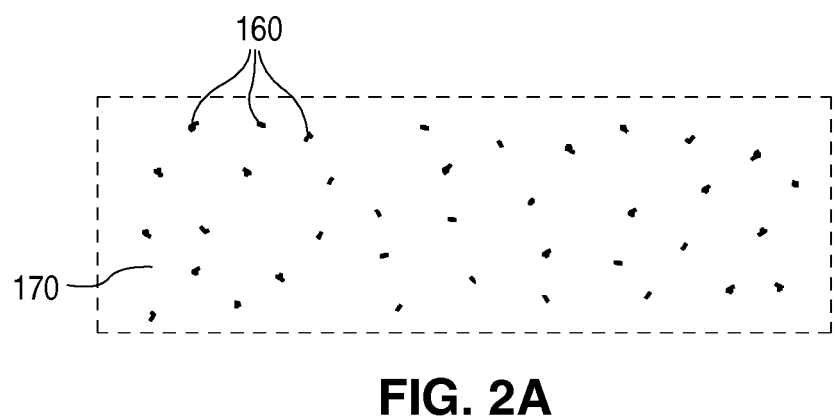
FIG. 2A depicts a schematic close-up view of the section depicted in FIG. 1B for a stent made from a polymer/bioceramic composite.
Figure 2B:
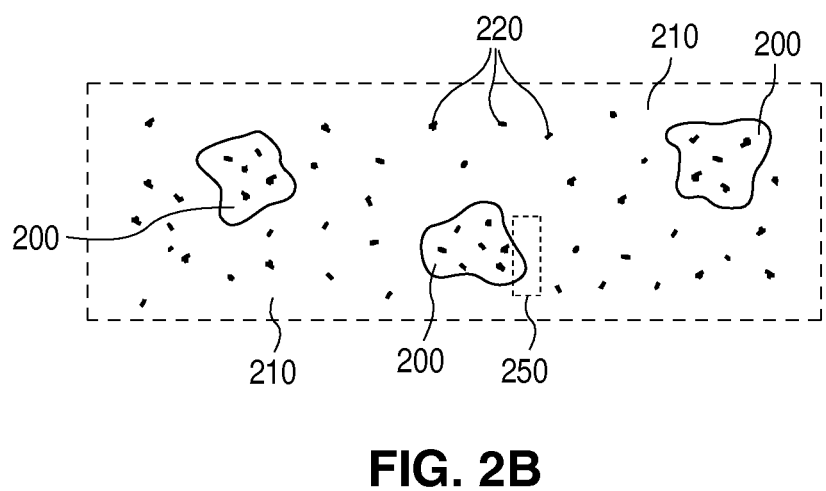
FIG. 2B depicts a schematic close-up view of the section depicted in FIG. 1B made from a polymer blend/bioceramic composite.

FIG. 1B depicts a section of a segment 110 of strut 105 from the stent depicted in FIG. 1A. FIGS. 2A-B depict a two alternative microscopic views of a portion 140 of segment 110 of the strut as depicted in FIG. 1B. In FIG. 2A, bioceramic particles 160 are mixed or dispersed within a matrix polymer 170.

An exemplary embodiment of a polymer/bioceramic composite includes a matrix polymer of PLLA-PGA-PCL copolymer (LPLGC) with a weight percent ratio of 80% LLA, 10% GA, and 10% CL. The weight percent ratio of polymer to hydroxyapatite bioceramic particles is 100:3. The mixture is extruded to form tubing, the tubing can be radially expanded, and then the expanded tubing is cut into a stent. The expected degradation time of the exemplary composite stent is about 10-14 months.

Another exemplary embodiment of a polymer/bioceramic composite includes a matrix polymer of PLLA-PGA-PCL copolymer (LPLGC) with a weight percent ratio of 80% LLA, 17% GA, and 3% CL. The weight percent ratio of polymer to nano calcium sulfate bioceramic particles is 100:3. The mixture is extruded to form tubing, the tubing can be radially expanded, and then the expanded tubing is cut into a stent. The expected degradation time of the composite stent is about 8-10 months.

FIG. 2B depicts a discrete polymer phase 200 mixed or dispersed within a continuous polymer phase 210. Bioceramic particles 220 are mixed or dispersed within discrete polymer phase 200 and continuous polymer phase 210.

Figure 3:
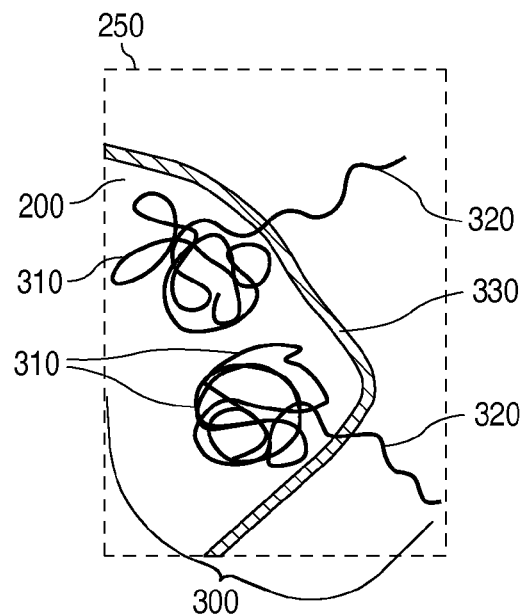
FIG. 3 depicts a schematic close-up view of an interface between a discrete polymer phase and a continuous polymer phase from FIG. 2B.

FIG. 3 depicts a schematic close-up view of section 250 including an interface between discrete phase 200 and continuous polymer phase 210. A modifier polymer 300 is shown to have discrete phase segments 310 and anchor segments 320. Region 330 is meant to delineate the boundary between discrete phase 200 and continuous phase 210. Anchor segments 320 are shown to be phase separated from discrete phase 200 into continuous phase 210.

It is believed that when a device is placed under stress, the discrete phase tends to absorb energy when a fracture starts to propagate through a structural element. Crack propagation through the continuous phase may then be reduced or inhibited. As a result, fracture toughness of the blend of the matrix polymer and the modifier polymer, and thus the structural element tends to be increased. Furthermore, the anchor segments tend to increase the adhesion between the discrete phase and the continuous phase. Thus, the anchor segments facilitate energy transfer through interfaces and between phases.

It is believed that bioceramic particles increase fracture toughness of the matrix polymer through dispersion of stress and strain in a device over a larger volume. The stress and strain can be divided into many small interactions involving numerous individual particles. For example, when a crack is initiated in the material and starts traveling through the matrix polymer, the crack is dispersed or is broken up into finer and finer cracks due to interaction with the particles. Thus, the particles tend to dissipate the energy imparted to the device by the applied stress that caused the crack. In exemplary embodiments, a composite can have at least 0.1 wt %, between 0.1 and 2 wt %, between 2 and 10 wt %, or between 10 and 20 wt % bioceramic particles.

In general, the increase in the toughness arising from the bioceramic particles is directly proportional to the size of the particles. For a give weight ratio of particles to matrix, as the size of the particles decreases the number of particles dispersed throughout the device per unit volume also increases. Thus, the number of particles to disperse the energy of applied stress to the device increases. Therefore, it is advantageous to use nanoparticles to increase the toughness of the polymer. It has been shown that the fracture toughness of a polymeric material can be improved by using nanoparticles as a discrete or reinforcing phase in a composite. J. of Applied Polymer Science, 94 (2004) 796-802.

In general, it is desirable for the bioceramic particles to be uniformly dispersed throughout the biodegradable matrix polymer or the polymer blend. A more uniform dispersion of the particles results in more uniform properties of the composite and a device fabricated from the composite. For example, a uniform dispersion can result in a uniform increase in toughness and modulus and modification of degradation rate. In some embodiments, the bioceramic particles are uniformly or substantially uniformly dispersed within the biodegradable matrix or polymer blend.

In some embodiments, the discrete phase segments of the modifier polymer can include units or functional groups that are known to form polymers that have a higher fracture toughness than a matrix polymer such as PLLA or LPLG. The discrete phase segments can form a discrete phase that is more flexible and has a lower modulus than the matrix polymer of the continuous phase. In one embodiment, the discrete phase segments of the modifier polymer can be a rubbery or elastomeric polymer. In an embodiment, the discrete phase segments of the modifier polymer have a Tg below body temperature.

As indicated above, biodegradable polymers having a relatively high fracture toughness include, but are not limited to, polycaprolactone (PCL) and poly(trimethylene carbonate) (PTMC). PCL and PTMC are immiscible in exemplary matrix polymers such as PLLA and in LPLG. Thus, some embodiments of the discrete phase segments of the modifier polymer can include CL and/or TMC units. The fraction of the CL and/or TMC units can be adjusted to be high enough that the discrete phase segments are immiscible in the PLLA or LPLG.

As indicated above, a matrix polymer, such as PLLA, can have a degradation rate that is slower than desired for certain stent treatments. Thus, in additional embodiments the modifier polymer can include hydrolytically degradable units or functional groups that provide desired degradation characteristics. In some embodiment, the discrete phase segments of the modifier polymer can include functional groups or units that increase water penetration and content in the discrete phase and in the continuous phase. In particular, the discrete phase segments can include monomers that have a higher affinity for water and/or are more hydrolytically active than the matrix polymer. For example, the discrete phase segments can include hydrolysis-enhancing functional groups such as GA units which are faster degrading than L-lactide units.

In other embodiments, the discrete phase segments can include functional groups that increase the fracture toughness of the polymer blend and functional groups that increase the degradation rate of the polymer blend. Thus, the discrete phase segments can include toughness-enhancing and hydrolysis-enhancing functional groups. In an embodiment, the discrete phase segments can include both CL and GA monomers. In particular, the discrete phase segments can be poly(glycolide-co-ε-caprolactone) (P(GA-co-CL)). P(GA-co-CL) discrete phase segments can have alternating or random GA and CL monomers. The faster degrading GA monomers can increase the degradation rate of the polymer blend by increasing the equilibrium water content and penetration into the structural element. The acidic and hydrophilic degradation products of the GA segments also act to increase the degradation rate of the polymer blend.

In some embodiments, the flexibility and degradation rate of the discrete phase segments can be adjusted by the ratio of hydrolysis-enhancing and toughness-enhancing units. As the ratio of CL, for example, increases in P(GA-co-CL) segments, the polymer becomes more flexible and tougher. The Tg of the discrete phase segments can be tuned to a desired value by adjusting the ratio of component monomers. For example, the Tg of the discrete phase may be engineered to be less than a body temperature to provide a more flexible discrete phase under physiological conditions. Additionally, the degradation rate of the discrete phase segments, and thus the blend, can be increased by increasing the fraction of GA in the discrete phase segments. In exemplary embodiments, the P(GA-co-CL) segments can have greater than 1 wt %, 5 wt %, 20 wt %, 50 wt %, 70 wt %, 80 wt %, or 90 wt % GA monomer.

In one embodiment, the modifier polymer can include P(GA-co-CL)-b-PLLA or PLLA-b-P(GA-co-CL). In each case, the discrete phase segment is P(GA-co-CL) and the anchor segment is PLLA. In a binary polymer blend of a modifier polymer of P(GA-co-CL)-b-PLLA and/or PLLA-b-P(GA-co-CL) with a matrix polymer of PLLA, the PLLA anchor segment of the modifier polymer can phase separate into the PLLA matrix of the continuous phase. The PLLA anchor segment can bind the discrete phase with the continuous phase, facilitating the increase in the fracture toughness of the polymer blend.

In exemplary embodiments, the polymer blend/bioceramic composite can include about 1-30 wt % or 5-20 wt % of a modifier polymer and about 75-95 wt % of matrix polymer. The polymer blend/bioceramic composite can further include at least about 0.1 wt %, between 0.1 and 1 wt %, between 1 and 10%, or between 10 and 20 wt % bioceramic particles.

Additionally, the anchor segment of the modifier polymer can be selected so that the anchor segment is miscible with the matrix polymer. In one embodiment, the anchor segment can have the same functional group composition as the matrix polymer. In another embodiment, the anchor segment can have a functional group composition different from the matrix polymer, but close enough so that the anchor segment is miscible with the matrix polymer. In another embodiment, the anchor segment can have composition different from the matrix polymer with the anchor segments being miscible with the matrix polymer.

Some embodiments can include a matrix polymer of PLLA and anchor blocks that include 100% L-lactide units or both L-lactide and GA units. Other embodiments can include a matrix polymer of LPLG and anchor blocks that include 100% L-lactide units or both L-lactide and GA units.

In some embodiments, a blend for fabricating an implantable medical device can be a ternary blend of the matrix polymer, a modifier polymer with discrete phase segments and an anchor block, and a discrete phase copolymer composed of discrete phase segments of the modifier polymer. The matrix polymer can form a continuous phase and the discrete phase copolymer can form a discrete phase within the continuous phase. The modifier polymer may act as a compatibilizer for the matrix polymer and the discrete phase copolymer by facilitating adhesion between the discrete and continuous phases. In one embodiment, the copolymer with discrete phase segments is a majority of the discrete phase.

In an exemplary embodiment, a ternary blend can include PLLA as the matrix polymer; P(GA-co-CL) copolymer; and P(GA-co-CL)-b-PLLA and/or PLLA-b-P(GA-co-CL) as the modifier polymer. In such embodiments, P(GA-co-CL) copolymer is in the discrete phase along with P(GA-co-CL) segments of the modifier polymer. PLLA of the modifier polymer phase separates into the PLLA continuous phase.

In another exemplary embodiment, a ternary blend can include LGLG as the matrix polymer; P(GA-co-CL) copolymer; and P(GA-co-CL)-b-LPLG and/or LPLG-b-P(GA-co-CL) as the modifier polymer. In such embodiments, P(GA-co-CL) copolymer is in the discrete phase along with P(GA-co-CL) segments of the modifier polymer. LPLG of the modifier polymer phase separates into the LPLG continuous phase.

In exemplary embodiments, a ternary polymer blend for a polymer blend/bioceramic composite can include about 5-25 wt % of a discrete phase copolymer, about 0.5-2 wt % of a modifier polymer, and about 75-95 wt % of matrix polymer. The matrix polymer can be PLLA, the discrete phase copolymer can be P(GA-co-CL), and the modifier polymer can be PLLA-b-P(GA-co-CL) and/or PLLA-b-P(GA-co-CL). The polymer blend/bioceramic composite can include at least 0.1 wt %, between 0.1 and 1 wt %, between 1 and 10%, or between 10 and 20 wt % bioceramic particles.

In further embodiments, the degradation rate and degradation time of an implantable medical device formed at least in part from polymer/bioceramic composite can be adjusted by using different types of bioceramic particles. As used herein, two bioceramic particles are a "different type" if they are composed of a different material. As previously discussed, some types of bioceramic particles can modify the degradation rate of hydrolytically degradable polymers. Such bioceramic particles are referred to herein as degradation-modifying particles. Thus, bioceramic particles dispersed within a polymer of an implantable medical device can modify the degradation rate and degradation time of the device.

As discussed above, the degradation rate of hydrolytically degradable polymers can be modified or influenced by moisture content or moisture absorption rate and the local pH. The degradation rate is increased by an increase in moisture content or moisture absorption rate. The degradation rate tends to increase as the pH decreases.

Thus, dispersed bioceramic particles having acidic degradation by-products ("acidic" bioceramic particles) can increase the degradation rate of a polymer of a device, decreasing the degradation time of the device. Additionally, dispersed bioceramic particles having basic degradation products ("basic" bioceramic particles) can decrease the degradation rate of the composite polymer, which increases the degradation time of the device. An example cited above of a bioceramic with acid degradation by-products is calcium sulfate. Hydroxyapatite has basic degradation products.

In addition, bioceramic particles having hydrophilic surface groups ("hydrophilic" bioceramic particles), such as hydroxyl groups, can increase moisture content which increases degradation rate and decreases degradation time of a device. An example of a bioceramic particle with surface hydroxyl groups is fluorine mica.

Alternatively, some bioceramic particles do not have basic or acidic degradation by-products or hydrophilic surface groups. Such bioceramic particles may have little or no effect on the degradation rate or degradation time of a device. Macromol. Mater. Engin. 2003, 288, 203-208. An example of such a material is montmorillonite.

In some embodiments, at least a portion of an implantable medical device can be formed from a bioceramic/polymer composite having a plurality of bioceramic particles dispersed within a polymer with at least two types of bioceramic particles. In certain embodiments, the different types have a different effect on the degradation rate of the polymer. "Different effect" can correspond to a difference in the direction (increase or decrease) of change that in degradation rate caused by the presence of a bioceramic particles in a polymer. "Different effect" can also correspond to a difference in the degree of change that in degradation rate caused by the presence of a bioceramic particles in a polymer. For example, two types of bioceramic particles have a different effect if the both accelerate the degradation rate of the composite polymer, but one accelerates it more than the other.

Therefore, the degradation rate and degradation time of the device depends on the ratio of the different types of bioceramic particles. In certain embodiments, the degradation rate and degradation time of a composite portion of device can be adjusted or tuned to selected values by changing the ratio of the different types of bioceramic particles. In exemplary embodiments, the ratio of the types of particles can be adjusted so that the degradation time of the scaffold is less than 18 months, 12 months, 6 months, or 3 months.

Figure 4:
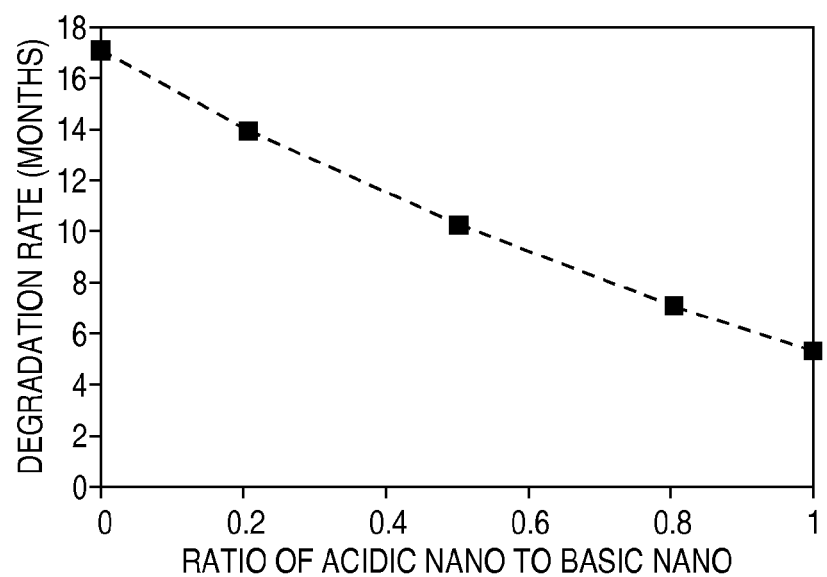
FIG. 4 depicts a plot of the expected dependence of degradation rate the ratio of acidic to basic particles in a PLLA/modifier polymer/bioceramic composite stent.

In general, the use of more than one type of bioceramic particles provides the capability of adjusting the degradation rate with little or no change to the mechanical properties of a composite. As discussed above, a matrix polymer can be modified or the fraction of modifier polymer in the composite polymer can be modified to change the degradation rate of the composite polymer. However, such modifications can also alter the mechanical properties of the composite, possibly in an unfavorable manner. For example, an increase in the fraction of modifier polymer in the composite can result in an undesirable low modulus of the composite In some embodiments, the composite portion of a device can include bioceramic particles that increase the degradation rate and bioceramic particles that decrease the degradation rate. In one such embodiment, the composite portion includes both acidic and basic bioceramic particles. As the ratio of acidic to basic bioceramic particles increases from zero to one, it is expected that the degradation rate of the composite portion increases and the degradation time decreases. In another such embodiment, the composite portion can include basic and hydrophilic particles. As the ratio of hydrophilic to basic bioceramic particles increases from zero to one, it is expected that the degradation rate of the composite portion increases and the degradation time decreases. In an exemplary embodiment, as the ratio of acidic to basic bioceramic particles goes from zero to one for a PLLA/modifier polymer/bioceramic composite stent, it is expected that the degradation time can range between 17 and five months. FIG. 4 depicts a plot of the expected dependence of degradation rate the ratio of acidic to basic particles in a PLLA/modifier polymer/bioceramic composite stent.

In other embodiments, the composite portion can include bioceramic particles that increase the degradation rate and bioceramic particles that have little or no effect on the degradation rate of the composite polymer ("neutral particles"). For example, as the ratio of acidic or hydrophilic to neutral bioceramic particles increases from zero to one, it is expected that the degradation rate of the composite portion increases and the degradation time decreases.

In other embodiments, the composite portion can include bioceramic particles that decrease the degradation rate and neutral particles. For example, as the ratio of neutral bioceramic particles to basic particles increases from zero to one, it is expected that the degradation rate increases and the degradation time decreases.

In some embodiments, selected types of degradation-modifying particles in a composite can be configured to modify the degradation rate of the polymer during a selected time frame of degradation. In exemplary embodiments, the selected time frame of degradation can be a time period during which a composite portion of a device, such as a stent scaffolding, is required to maintain vascular patency ("patency" period). Such a time period can be up 1 month, 3 months, 5 months, 7 months, 10 months, 12 months, or 15 months after implantation. In other exemplary embodiments, the selected time frame of degradation can be a time period after the patency period, during which a stent completely absorbs and disintegrates ("disintegration" period). Such a time period can be after 1 month, 3 months, 5 months, 7 months, 10 months, 12 months, or 15 months after implantation.

In certain embodiments, the degradation of selected degradation-modifying particles can be reduced or prevented during a selected time frame by coating or encapsulating the particles with a bioabsorbable polymer. The encapsulating polymer can reduce or prevent exposure of the bioceramic particle to bodily fluids for a period of time which cause degradation of the bioceramic particle. As a result, the encapsulating polymer reduces or prevents the bioceramic particle from modifying the degradation of the composite polymer for the period of time. For acidic and basic bioceramic particles, the bioabsorbable polymer can reduce or prevent degradation of the particles, thus preventing, release of degradation by-products that increase or decrease, respectively, the degradation rate of the composite polymer. For hydrophilic particles, the bioabsorbable polymer can shield the hydrophilic surface groups from the composite polymer, thus reducing or preventing the increase in degradation rate due to the hydrophilic groups.

Furthermore, the duration and degree of shielding provided by the encapsulating polymer can be adjusted by the type of encapsulating polymer used. It is expected that as the degradation rate of the encapsulating polymer decreases, the longer is the duration of shielding from the degradation-modifying polymer.

Bioabsorbable polymers spanning the range of behavior from idealized surface erosion to a high degree of bulk erosion can be used as encapsulating polymers. The degree of shielding from degradation of the encapsulated bioceramic particle depends on the degree of bulk erosion of an encapsulating polymer. A bulk eroding encapsulating polymer allows some bodily fluid exposure of an encapsulated particle due to diffusion through the encapsulating polymer. Thus, there is some degradation of the encapsulated particle prior complete absorption of the encapsulating polymer. This degradation can then modify the degradation of the composite polymer.

As the bulk eroding encapsulating polymer erodes, it is expected that the degradation of the encapsulated particle increases with time, which causes increased modification of the degradation rate of the composite. For example, the release rate of degradation by-products from an acidic or basic particle increases as the bulk eroding polymer erodes. As the degree of bulk erosion of the encapsulating polymer increases, the degree of shielding decreases. Thus, accelerating or slowing effect that a bioceramic particle has on a composite polymer can occur gradually through the use of a bulk eroding polymer.

Alternatively, a polymer close to an idealized surface eroding polymer, which has no bulk erosion, can almost completely shield a bioceramic particle from bodily fluid exposure until the encapsulating polymer is eroded from the surface of the polymer. Thus, the effect of the bioceramic particle on the composite polymer occurs in a step-wise or discrete fashion once the encapsulating polymer erodes away.

Encapsulated bioceramic particles can be made by methods known to those of skill in the art. An exemplary method for making encapsulated bioceramic particles can include forming a suspension of bioceramic particles in a non-organic fluid, such as an aqueous solution. A separate solution of an encapsulating polymer in an organic solvent is prepared. The polymer solution and the suspension are then combined and mixed vigorously, for example, using a high speed mixer. The bioceramic particles will be encapsulated by the encapsulating polymer. The encapsulated bioceramic particles can then be separated from the solution with an ultracentrifuge.

An exemplary encapsulating polymer for use with a PLLA or LPLG matrix polymer, for example, can include polyanhydride and poly(ester amide). A suitable solvent for polyanhydride or poly(ester amide) can include chloroform or tetrahydrafuran.

In some embodiments, the degradation of the composite polymer can be reduced during a selected time period and accelerated during a second selected time period. One such embodiment is slowing the degradation during a patency period and accelerating the degradation during a disintegration period. In such an embodiment, the composite can include basic particles and encapsulated acidic and/or hydrophilic particles. The basic particles can slow the degradation during a patency period to maintain the mechanical properties of the stent. The encapsulated acidic or hydrophilic particles can accelerate the degradation once support is no longer needed to hasten the disintegration and complete absorption of the stent.

In an alternative embodiment, the degradation of the composite polymer can be substantially unmodified during a selected time period and accelerated during a second selected time period. In such an embodiment, rather than basic particles, particles that have little or no effect on degradation of the composite polymer can be used.

Figure 5:
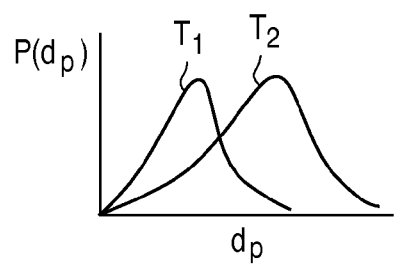
FIG. 5 depicts probability density functions of particle size distributions for two different types of particles.

In some embodiments, at least a portion of an implantable medical device can be formed from a bioceramic/polymer composite having at least two different types of bioceramic particles that have different particle size distributions. In general, a plurality of bioceramic particles of the same type are polydisperse, i.e., not all the same size. "Size" refers to a characteristic dimension of a particle, for example, a diameter. The polydispersity can be characterized and quantified in several ways using a particle size distribution. The particle size distribution (PSD) refers to the relative percentage by weight or number of each of the different size fractions of particulate matter. The PSD can be represented graphically by a probability density function, as shown in FIG. 5. $T_1$ and $T_2$ are probability density functions of particle size distributions for two different types of particles.

The properties of the particles can be quantified by particle size parameters including the mean particle size, median particle size, and the mode. Additionally, the breadth of a PSD can be characterized, for example, by the standard deviation of the PSD and by the maximum and minimum particle sizes. For a plurality of particles, the mean or arithmetic average particle size is the sum of all the particles' sizes divided by the number of particles. The median particle size is the diameter for which 50% of the total particles are smaller and 50% are larger. The mode is the most frequent particle size and corresponds to the peak of a particle size distribution. The mode size can be obtained by setting the derivative of the probability density function to zero and solving for the diameter. For a symmetrical distribution, the mean, median, and mode have the same value. In addition, the standard deviation of the PSD quantifies the breadth of the distribution. The higher the standard deviation, the broader is the distribution of particles sizes.

In general, for a given mass of biodegradable particles, the smaller the particle size, the faster is the erosion rate of the particles. Erosion rate refers to the mass eroded per unit time. This is due to a greater surface area that is exposed to bodily fluids. Thus, for a composite that can include two different types of particles, the erosion rate of a selected type can be increased with respect to the other type by suitable selection of the PSD (smaller particles) of the selected type.

Furthermore, since decreasing the size of particles increases erosion rate, the particles erode away faster. As the particles erode, it is expected that the cumulative erosion rate decreases. The cumulative erosion rate is the mass eroded from all particles of a given type per unit time. The decrease in the cumulative erosion rate also means that the release of degradation by-products will decrease with time and occur over a short time period if the particle sizes are decreased. Thus, the PSD of a type of particle can be selected so that its cumulative erosion rate with time is high during a selected period and low during a later period. For example, basic particles can have a PSD such that the release of basic degradation by-products is high during a patency period and lower during a disintegration period.

Additionally, the time frame of the degradation of a type of particle depends in part on the breadth of the distribution. The narrower the PSD, it is expected that the time frame during which particles erode is also narrower.

In some embodiments, the PSD of two types of degradation-modifying bioceramic particles in a composite can be selected so that the effect of a first type dominates the other during an initial time frame and a second type is dominant in a later time frame. In particular, the sizes of the first type of particles is small enough that the first type has a higher release rate of by-products initially. The sizes of the second type are large enough to allow a higher release rate of by-products in a later time period. The initial time period can be a patency period and the later time period can be a disintegration period. In such embodiments, the particles can be designed to have a particle size parameter (e.g., mean, median, mode) and a breadth parameter (e.g., standard deviation) so that a desired degradation behavior is obtained during the selected time frame.

In particular embodiments, the plurality of bioceramic particles in a composite can include acidic particles and basic particles, the acidic particles and basic particles having different particle size distributions. In some embodiments, the PSD of the basic particles is selected so that a cumulative erosion rate of the basic particles is faster than the acidic particles upon implantation. In such an embodiment, PSD of the basic particles is selected so that a cumulative erosion rate, and thus, release rate of basic by-products, of the basic particles is greater than a cumulative erosion rate, and thus, release rate of acidic by products, of the acidic particles during a selected time period, such as a patency period. In further embodiments, the basic particles can have a cumulative erosion rate that is less than a cumulative erosion rate of the acidic particles after a patency period. In such embodiments, the combined influence of the bioceramic particles is that the degradation rate of the composite polymer is reduced during the patency period and accelerated after the patency period.

In such embodiments, the basic particles can have a smaller average diameter than the acidic particles. For example, the basic particles can have an average diameter between 5 nm and 100 nm and the acidic particles can have average diameters between 200 and 400 nm. In some embodiments, the maximum particle size of the basic particles is less than the maximum particle size of the acidic particles. In other embodiments, the maximum particle size of the basic particles is less than the maximum and minimum particle sizes of the acidic particles.

It may be also be desirable for bioceramic particles to slow the degradation of a stent during the patency period and for bioceramic particles to have little or no effect on degradation during a disintegration period. In such embodiments, the composite can include particles that have little or no effect on the degradation of the composite polymer rather than acidic or hydrophilic particles.

In some embodiments, a modifier polymer, such as P(GA-co-CL)-b-PLLA or P(GA-co-CL)-b-LPLG, can be formed by solution-based polymerization. Other methods used to form the modifier polymers are also possible, such as, without limitation, melt phase polymerization. In solution-based polymerization, all the reactive components involved in the polymerization reaction are dissolved in a solvent.

Figure 6A:
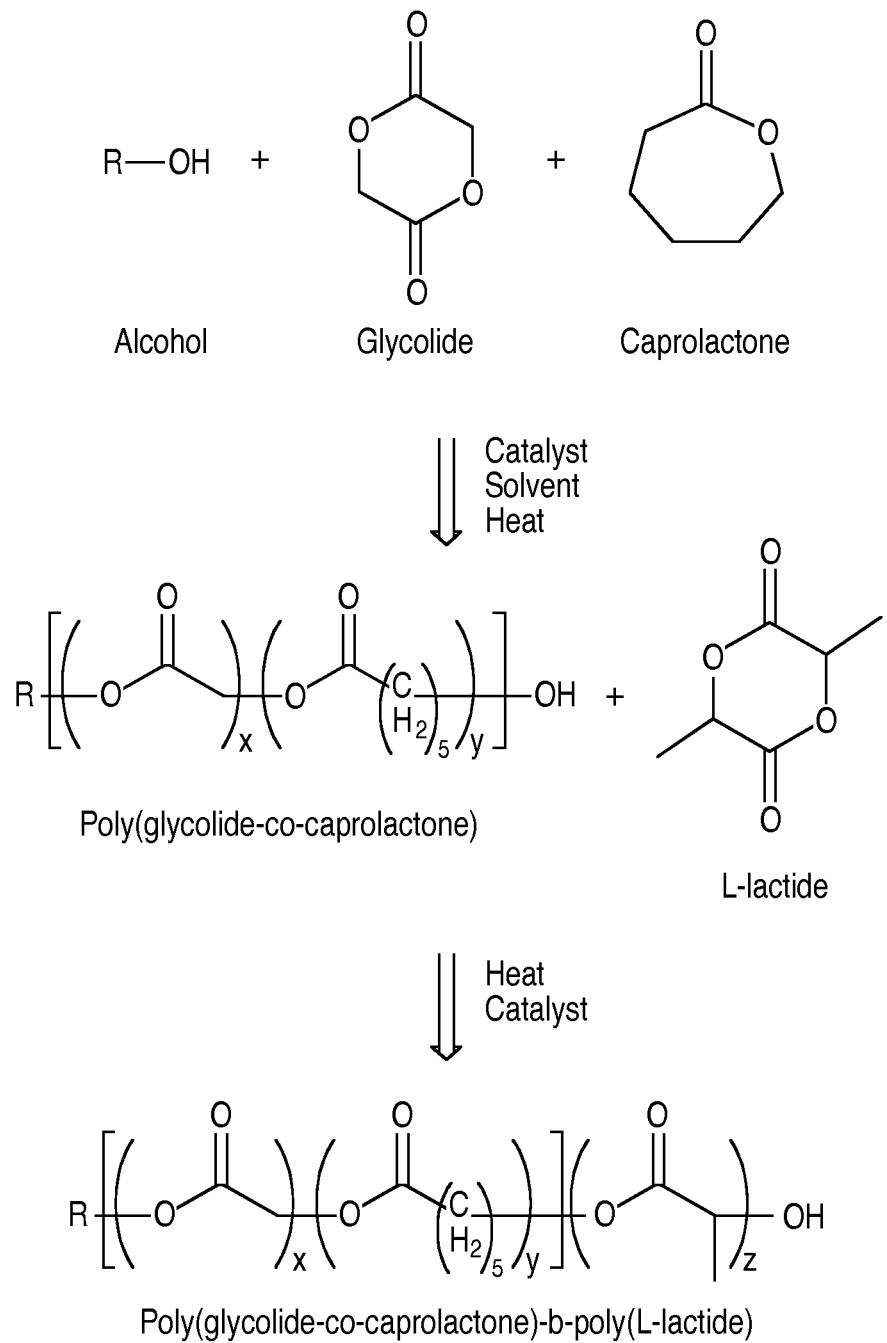
FIG. 6A depicts a synthesis scheme of a modifier polymer with a PLLA anchor segment.

To prepare P(GA-co-CL)-b-PLLA copolymer, P(GA-co-CL) may be prepared first by solution polymerization and then employed as a macro-initiator to initiate the polymerization of L-lactide monomers to form the PLLA segment, as illustrated in FIG. 6A. Specifically, P(GA-co-CL) segments are formed first by mixing GA monomers and CL monomers with a solvent to form a solution. In the solution, the GA and CL monomers react to form P(GA-co-CL). L-lactide monomers can then be added to the solution or another solution containing the formed P(GA-co-CL). The L-lactide monomers react with P(GA-co-CL) to form P(GA-co-CL)-b-PLLA.

Figure 6B:
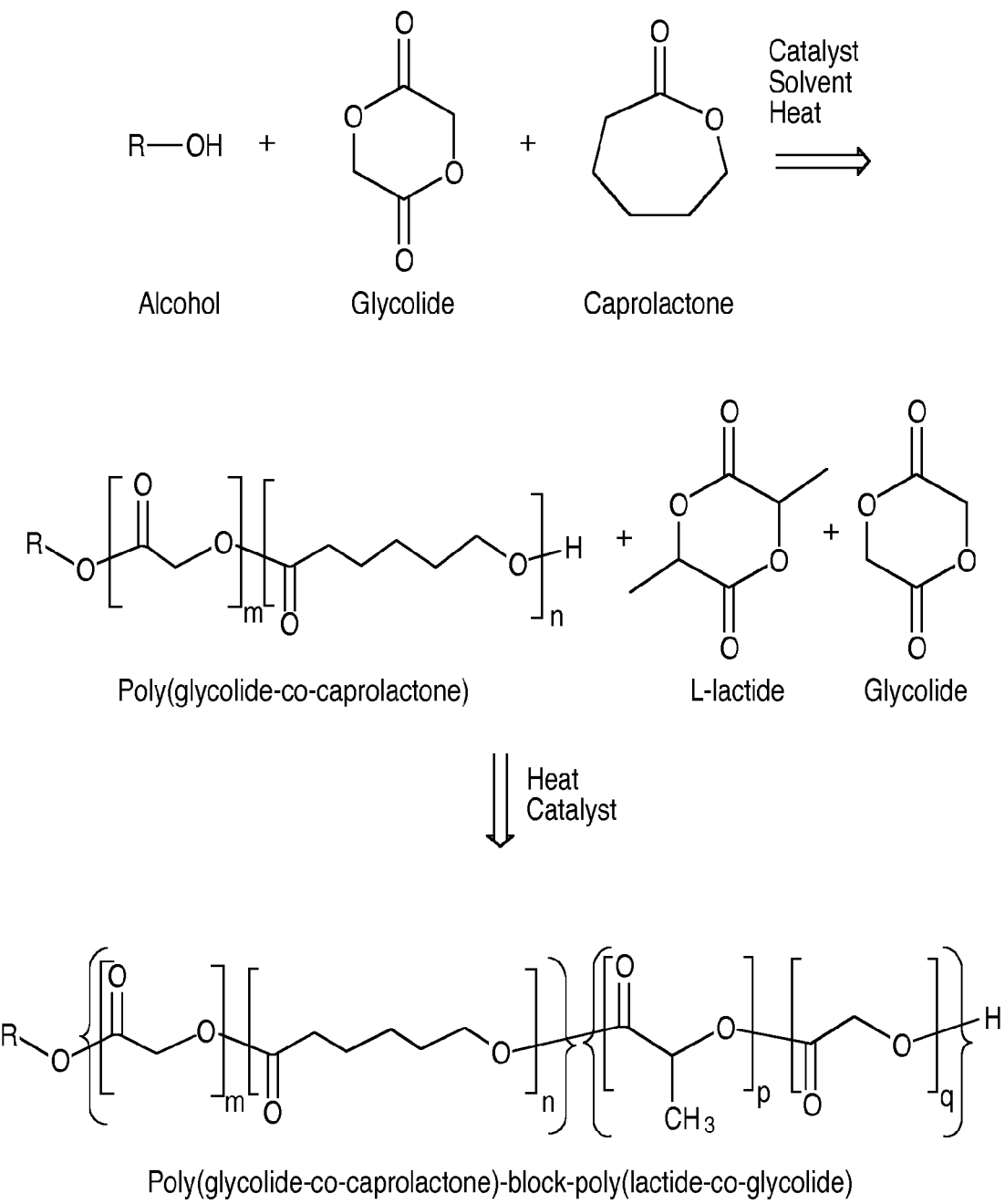
FIG. 6B depicts a synthesis scheme of a modifier polymer with a LPLG anchor segment.

To prepare P(GA-co-CL)-b-LPLG copolymer, P(GA-co-CL) may be prepared first by solution polymerization and then employed as a macro-initiator to initiate the polymerization of L-lactide and glycolide monomers to form the LPLG segment, as illustrated in FIG. 6B. As in FIG. 6A, P(GA-co-CL) segments are formed first by mixing GA monomers and CL monomers with a solvent to form a solution. In the solution, the GA and CL monomers react to form P(GA-co-CL). L-lactide and glycolide monomers can then be added to the solution or another solution containing the formed P(GA-co-CL). The L-lactide and glycolide monomers react with P(GA-co-CL) to form P(GA-co-CL)-b-LPLG.

In one embodiment, the L-lactide monomers react in the same solution as the solution used to form P(GA-co-CL). Alternatively, the L-lactide monomers can react in a solution having a different solvent than the solution for forming P(GA-co-CL). The solvent(s) for forming the PLLA anchor segment can be selected so that the P(GA-co-CL) copolymer is soluble in the solvent(s) so that the copolymer can further copolymerize with L-lactide monomers.

In other embodiments, P(GA-co-CL)-b-PLLA can be formed by reacting P(GA-co-CL) copolymer swollen with a solvent with L-lactide monomers. One of skill in the art can select a solvent that swells but does not dissolve P(GA-co-CL). P(GA-co-CL) copolymer is swollen by a solvent after it is formed so that the P(GA-co-CL) copolymer can react with added L-lactide monomers.

In another embodiment, the synthesis of the PLLA-b-P(GA-co-CL) copolymer can be performed by first synthesizing the PLLA block. The L-lactide monomers can be mixed with a solvent to form a solution. GA monomers and CL monomers are added to a solution containing the PLLA that is formed to form PLLA-b-P(GA-co-CL) copolymer. The solution can be the same solution used to form the PLLA or a solution containing a different solvent.

In one embodiment, the solvent for use in synthesizing the copolymer is devoid of alcohol functional groups. Such alcohol groups may act as initiators for chain growth in the polymer. Solvents used to synthesize the copolymer include, but are not limited to, chloroform, toluene, xylene, and cyclohexane. Initiators to facilitate the synthesis of the copolymer include, but are not limited to, dodecanol, ethanol, ethylene glycol, and polyethylene glycol. Catalysts used to facilitate the synthesis of the copolymer include, but are not limited to, stannous octoate and stannous trifluoromethane sulfonate.

In some embodiments, the matrix polymer/bioceramic or polymer blend/bioceramic composite can be formed by melt blending. In melt blending the bioceramic particles are mixed with a polymer melt. The particles can be mixed with the polymer melt using extrusion or batch processing. A composite of the matrix polymer or polymer blend and bioceramic particles can be extruded to form a polymer construct, such as a tube. A stent can then be fabricated from the tube.

In one embodiment, the bioceramic particles can be combined with a matrix polymer or polymer blend in a powdered or granular form prior to melting of the polymer. The particles and polymer can be mixed using mechanical mixing or stirring such as agitation of the particles and polymer in a container or a mixer. The agitated mixture can then be heated to a temperature above the melt temperature of the matrix polymer or at least one of the polymers of the polymer blend in an extruder or using batch processing.

In further embodiments, a method of making a polymer blend/bioceramic composite for a medical device can include preparing the composite from a suspension of bioceramic particles and a polymer solution. A potential problem with the mechanical mixing or stirring techniques discussed above is that the polymer and particles may separate into regions or layers. This is particularly a problem with respect to smaller particles such as nanoparticles. Additionally, it may be difficult to obtain a uniform dispersion by mixing particles with a polymer melt since particles can agglomerate or form clusters. The mechanical mixing in an extruder or in batch processing may not be sufficient to break up the clusters, resulting in a nonuniform mixture of bioceramic particles and polymer blend. Bioceramic particles may be more uniformly dispersed in a composite formed from a suspension.

Certain embodiments of a method of forming an implantable medical device may include forming a matrix polymer/bioceramic or polymer blend/bioceramic composite from a suspension including bioceramic particles suspended in a polymer solution. A "suspension" is a mixture in which particles are suspended or dispersed in a fluid. The polymer solution can include a polymer dissolved in a fluid that is a solvent for the polymer. The particles can be mixed with the fluid before or after dissolving the polymer in the fluid. Various mechanical mixing methods known to those of skill in the art may be used to disperse the bioceramic particles in the suspension. In one embodiment, dispersing the particles can be facilitated by an ultrasonic mixer.

The method may further include combining the suspension with a second fluid that is a poor solvent for the polymer. At least some of polymer may precipitate upon combining the suspension solution with the second fluid. In some embodiments, at least some of the bioceramic particles may precipitate from the suspension with the precipitated polymer to form a composite mixture of bioceramic particles and the polymer. The precipitated composite mixture may then be filtered out of the solvent. The filtered composite mixture can be dried to remove residual solvent. For example, the composite mixture can be dried in a vacuum oven or by blowing heated gas on the mixture.

The polymer solution can include, for example, a matrix polymer in the case of a matrix polymer/bioceramic composite. In the case of a polymer blend/bioceramic composite the polymer solution can include a modifier polymer, a polymer of discrete phase segments, or a combination thereof dissolved in a solvent. Exemplary polymers may include, but are not limited to, PLLA, PDLA, LPLG, P(GA-co-CL), PGA, PTMC, P(GA-co-CL)-b-PLLA, and PLLA-b-P(GA-co-CL). Representative solvents for such polymers can include toluene and chloroform. Representative poor solvents for these polymers that may be used to precipitate the polymer can include methanol, ethanol, isopropanol, and various alkanes such as hexane or heptane.

It is believed that in a suspension including bioceramic nanoparticles, the particles can have strong interactions with polymer chains in solution which can result in particles becoming encapsulated or surrounded by polymer chains. Thus, when the polymer is precipitated from the solution, the interactions of the particles with the polymer can overcome interactions of the particles with the solution so that the particles precipitate with the polymer.

Additionally, it has been observed that both the degree of precipitation of particles and the degree of dispersion of particles within the precipitated polymer depend upon the amount of polymer dissolved in the solution. The degree of precipitation refers to the amount of particles that precipitate out of the suspension. The degree of dispersion of particles within the precipitated polymer refers to the degree of mixing of the particles with the precipitated polymer.

The amount of polymer can be quantified by the weight percent of the polymer in the suspension solution. In addition, the viscosity of the solution is also related to the amount of polymer in the solution. The higher the weight percent of dissolved polymer, the higher is the viscosity of the suspension solution.

For a given concentration of suspended particles, as weight percent of dissolved polymer or viscosity is reduced, the degree of precipitation of particles is reduced. This is likely due to the reduced interaction of the particles with the polymer chains. Thus, at lower weight percent of polymer or viscosity, the amount of particles precipitating can be relatively low.

Additionally, for a given concentration of suspended particles, as the weight percent of polymer or viscosity of the solution is increased beyond an observed range, the degree of dispersion of particles in the precipitated polymer tends to decrease. It is believed that at higher weight percent of polymer or higher viscosity, the interactions between polymer chains reduce the interaction of particles with polymer chains that cause particles to precipitate. For example, particles may be unable to move freely among the polymer chains.

A given suspension has a particular combination of type of particles, particle concentration, and solvent. For this given suspension, the polymer weight percent or viscosity can be varied to obtain both a desired degree of precipitation of particles and degree of dispersion of particles in the precipitated polymer. Thus, there may be a range of polymer weight percent or viscosity that can result in a desired degree of precipitation of particles and degree of dispersion of particles in precipitated polymer.

Additionally, the manner of combining the suspension with the poor solvent can also affect the degree of precipitation and degree of dispersion. For example, depositing a fine mist of small droplets of suspension into a poor solvent can more readily result in a desired degree of precipitation and degree of dispersion. Thus, the manner of combining the suspension with the poor solvent can influence the range of polymer weight percent or viscosity that results in a desired degree of precipitation and degree of dispersion.

Further embodiments of the method include conveying the composite mixture into an extruder. The composite mixture may be extruded at a temperature above the melting temperature of the polymers in the composite mixture and less than the melting temperature of the bioceramic particles. In some embodiments, the dried composite mixture may be broken into small pieces by, for example, chopping or grinding. Extruding smaller pieces of the composite mixture may lead to a more uniform distribution of the nanoparticles during the extrusion process.

The extruded composite mixture may then be formed into a polymer construct, such as a tube or sheet which can be rolled or bonded to form a tube. A medical device may then be fabricated from the construct. For example, a stent can be fabricated from a tube by laser machining a pattern in to the tube. In another embodiment, a polymer construct may be formed from the composite mixture using an injection molding apparatus.

Preparation of a desired amount of precipitated composite mixture may require a large amount of solvent and precipitant. Therefore, in some embodiments, it may be advantageous to melt blend precipitated composite mixture with an amount of polymer in an extruder or in a batch process. The polymer can be the same or a different polymer of the precipitated composite mixture. For example, a relatively small amount of precipitated composite mixture that has a weight percent of bioceramic particles higher than is desired can be prepared. The precipitated composite mixture may be melt blended with an amount of biodegradable polymer to form a composite mixture that has a desired weight percent of bioceramic particles.

In some embodiments, a composite for use in fabricating an implantable device can be formed by first forming a composite mixture of a matrix polymer and bioceramic particles. The composite mixture can be formed by precipitation of a matrix polymer from a suspension of bioceramic particles in a matrix polymer solution. In the case of a polymer blend composite, the composite mixture can then be mixed with a modifier polymer, for example, by extrusion. In one embodiment, a batch of the precipitated matrix polymer or polymer blend/bioceramic composite mixture can be formed with a higher weight percent of bioceramic particles than a target weight percent for a device. The batch can then be mixed with a matrix polymer or polymer blend to obtain a matrix polymer or polymer blend/bioceramic composite with the target weight percent of bioceramic particles. For example, a 100:1 composite containing PLLA and modifier polymer can be prepared by first making a batch of PLLA/bioceramic composite with a 2:1 ratio of PLLA to bioceramic particles. The 2:1 composite can then be mixed with PLLA and modifier polymer to obtain a 100:1 PLLA-modifier polymer blend/bioceramic composite.

In other embodiments, a polymer blend/bioceramic composite for use in fabricating an implantable device can be formed by first forming a composite mixture of a modifier polymer and bioceramic particles. The composite mixture can be formed by precipitation of a modifier polymer from a suspension of bioceramic particles in a modifier polymer solution. The composite mixture can then be mixed with a matrix polymer, for example, by extrusion. In one embodiment, a batch of the precipitated modifier polymer/bioceramic composite mixture can be formed with a higher weight percent of bioceramic particles than a target weight percent for a device. The batch can then be mixed with a matrix polymer and modifier polymer to obtain a polymer blend/bioceramic composite with the target weight percent of bioceramic particles. For example, a 100:1 composite containing PLLA and modifier polymer can be prepared by first making a batch of modifier polymer/bioceramic composite with a 2:1 ratio of modifier polymer to bioceramic particles. The 2:1 composite can then be mixed with PLLA and modifier polymer to obtain a 100:1 PLLA-modifier polymer blend/bioceramic composite.

In some embodiments, the bioceramic particles in the composite can be bioabsorbable. The bioabsorbable bioceramic particles can increase the degradation rate of the composite and the degradation time of a device. In an embodiment, the degradation time of a composite device can be tuned and/or adjusted to a desired time frame. As bioceramic particles erode within the polymeric matrix, the porosity of the matrix polymer or polymer blend increases. The increased porosity increases the diffusion rate of moisture through the matrix polymer or polymer blend, and thus, the equilibrium moisture content of the matrix polymer or polymer blend. As a result, the degradation rate of the matrix polymer or polymer blend is increased. The porous structure also increases the transport of degradation products out of the matrix, which also increases the degradation rate of the matrix polymer or polymer blend.

In certain embodiments, the degradation rate and degradation time of the device can be tuned or controlled through variables such as the type of bioceramic material and the size and shape of particles. In some embodiments, bioceramic materials can be selected to have a higher degradation rate than the polymer blend. The faster the degradation rate of the bioceramic material, the faster the porosity of the matrix polymer or polymer blend increases which results in a larger increase in the degradation rate of the matrix polymer or polymer blend. Additionally, the size of the particles influences the time for erosion of the particles. The smaller the particles, the faster the erosion of the particles because of the higher surface area per unit mass of particles.

For example, nanoparticles may have a relatively fast erosion rate compared to microparticles. Additionally, elongated particles, such as fibers, may tend to erode faster on a per unit mass basis due to the higher surface area per unit mass of the particle. Also, short fibers may tend to erode faster than longer fibers. Short fibers refer to long fibers than have been cut into short lengths. In some embodiments, the short fibers may be made by forming fibers as described above, and cutting them into short lengths. In one embodiment, a length of at least a portion of the short fibers is substantially smaller than a diameter of the formed tube. For example, in some embodiments, the short fibers may be less than 0.05 mm long. In other embodiments, the short fibers may be between 0.05 and 8 mm long, or more narrowly between 0.1 and 0.4 mm long or 0.3 and 0.4 mm long.

Furthermore, the size and distribution of pores created by erosion of bioceramic particles can also influence the degradation rate and time of the matrix polymer or polymer blend. Smaller particles, such as nanoparticles, create a porous network that exposes a larger volume of the matrix polymer or polymer blend to bodily fluid than larger particles, like microparticles. As a result the degradation rate and time of the matrix may be higher when nanoparticles are used rather than microparticles.

Through appropriate selection of the type of material for the particles and the size and shape of the particles, the particles and a composite device can be designed to have selected erosion rates and degradation time. For example, the particles can designed erode away in several minutes, hours, days, or a month upon exposure to bodily fluid.

As indicated above, many biodegradable polymers degrade by the mechanism of hydrolysis. The rate of the hydrolysis reaction tends to increase as the pH decreases. Since the degradation products of such polymers as polylactides are acidic, the degradation products have an autocatalytic effect. Therefore, the pH of the degradation products of the bioceramics can also affect the degradation rate of a device. Therefore, bioceramic particles with acidic degradation by-products may further increase the rate of degradation of a matrix polymer or polymer blend.

For example, tricalcium phosphate releases acidic degradation products. Thus, some embodiments may include a composite including a bioceramic having acidic degradation products upon exposure to bodily fluids. The acidic degradation products can increase the degradation rate of the polymer which can decrease the degradation time of the device.

In other embodiments, a composite can have bioceramic particles that have basic degradation products. For example, hydroxyapatite releases basic degradation products. The basic degradation products of the bioceramic particles can reduce the autocatalytic effect of the matrix polymer or polymer blend degradation by neutralizing the acidic degradation products of the polymer degradation. In some embodiments, the basic degradation products of the bioceramic particles can reduce the degradation rate of the matrix polymer or polymer blend.

In some embodiments, bioceramic particles may include an adhesion promoter to improve the adhesion between the particles and the matrix polymer or polymer blend. In one embodiment, an adhesion promoter can include a coupling agent. A coupling agent refers to a chemical substance capable of reacting with both the bioceramic particle and the matrix polymer or polymer blend of the composite material. A coupling agent acts as an interface between the polymer and the bioceramic particle to form a chemical bridge between the two to enhance adhesion.

The adhesion promoter may include, but is not limited to, silane and non-silane coupling agents. For example, the adhesion promoter may include 3-aminopropyltrimethoxysilane, 3-aminopropyltriethoxysilane, aminopropylmethyldiethoxy silane, organotrialkoxysilanes, titanates, zirconates, and organic acid-chromium chloride coordination complexes. In particular, 3-aminopropyltrimethoxysilane has been shown to facilitate adhesion between poly(L-lactide) and bioglass. Biomaterials 25 (2004) 2489-2500.

In some embodiments, the surface of the bioceramic particles may be treated with an adhesion promoter prior to mixing with the matrix polymer or polymer blend. In one embodiment, the bioceramic particles can be treated with a solution containing the adhesion promoter. Treating can include, but is not limited to, coating, dipping, or spraying the particles with an adhesion promoter or a solution including the adhesion promoter. The particles can also be treated with a gas containing the adhesion promoter. In one embodiment, treatment of the bioceramic particles includes mixing the adhesion promoter with solution of distilled water and a solvent such as ethanol and then adding bioceramic particles. The bioceramic particles can then be separated from the solution, for example, by a centrifuge, and the particles can be dried. The bioceramic particles may then used to form a polymer composite. In an alternative embodiment, the adhesion promoter can be added to the particles during formation of the composite. For example, the adhesion promoter can be mixed with a composite mixture during extrusion.

Representative examples of polymers that may be used to in the fabrication of an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. For the purposes of the present invention, the following terms and definitions apply:

Bioceramics can include any ceramic material that is compatible with the human body. More generally, bioceramic materials can include any type of compatible inorganic material or inorganic/organic hybrid material. Bioceramic materials can include, but are not limited to, alumina, zirconia, apatites, calcium phosphates, silica based glasses or glass ceramics, and pyrolytic carbons. Bioceramic materials can be bioabsorbable and/or active. Bioceramic materials can include bioabsorbable glass. A bioceramic is active if it actively takes part in physiological processes. Bioabsorbable glasses, including bioactive glasses, can be obtained from Mo-Sci Corporation in Hy Point North Rolla, Mo. A bioceramic material can also be "inert," meaning that the material does not absorb or degrade under physiological conditions of the human body and does not actively take part in physiological processes.

Illustrative examples of apatites and other calcium phosphates, include, but are not limited to hydroxyapatite ($Ca_{10}(PO_4)_6(OH)_2$), floroapatite ($Ca_{10}(PO_4)_6F_2$), carbonate apatide ($Ca_{10}(PO_4)_6CO_3$), tricalcium phosphate ($Ca_3(PO_4)_2$), octacalcium phosphate ($Ca_8H_2(PO_4)6-5H_2O$), octacalcium phosphate ($Ca_8H_2(PO_4)6-5H_2O$), calcium pyrophosphate ($Ca_2P_2O_7.2H_2O$), tetracalcium phosphate ($Ca_4P_2O_9$), and dicalcium phosphate dehydrate ($CaHPO_4.2H_2O$).

The term bioceramics can also include bioactive glasses that are bioactive glass ceramics composed of compounds such as $SiO_2$, $Na_2O$, $CaO$, and $P_2O_5$. For example, a commercially available bioactive glass, Bioglass®, is derived from certain compositions of $SiO_2$—$Na_2O$—$K_2O$—$CaO$—$MgO$—$P_2O_5$ systems. Some commercially available bioactive glasses include, but are not limited to:

45S5: 46.1 mol % SiO2, 26.9 mol % CaO, 24.4 mol % $Na_2O$ and 2.5 mol % $P_2O_5$;

58S: 60 mol % SiO2, 36 mol % CaO, and 4 mol % $P_2O_5$; and

S70C30: 70 mol % SiO2, 30 mol % CaO.

Another commercially available glass ceramic is A/W.

As indicated above, an implantable medical device such as a stent can be medicated by incorporating an active agent in a coating over the device or within the substrate of the device. In some embodiments, the ions released from bioceramics can have an additive therapeutic and/or a synergistic therapeutic effect to the active agent. For example, ions can be used in conjunction with anti-proliferative and/or anti-inflammatory agents.

Bioceramic particles can be partially or completely made from a biodegradable, bioabsorbable, or biostable ceramic. Examples of bioabsorbable bioceramics include various types of bioglass materials, tetracalcium phosphate, amorphous calcium phosphate, alpha-tricalcium phosphate, and beta-tricalcium phosphate. Biostable bioceramics include alumina and zirconia.

Various sizes of the bioceramic particles may be used in the composite. For example, the bioceramic particles can include, but are not limited to, nanoparticles and/or micro particles. A nanoparticle refers to a particle with a characteristic length (e.g., diameter) in the range of about 1 nm to about 1,000 nm. A microparticle refers to a particle with a characteristic length in the range of greater than 1,000 nm and less than about 10 micrometers. Additionally, bioceramic particles can be of various shapes, including but not limited to, spheres and fibers.

The composite of a structural element of a device may have between 0.01% and 10% of bioceramic particles by weight, or more narrowly, between 0.5% and 2% bioceramic particles by weight as compared to the polymeric component of the composite.

For the purposes of the present invention, the following terms and definitions apply:

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its Tg, a polymer tends to be brittle with a high modulus. As the temperature of a polymer is increased from below to above its Tg, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

"Solvent" is defined as a substance capable of dissolving or dispersing one or more other substances or capable of at least partially dissolving or dispersing the substance(s) to form a uniformly dispersed solution at the molecular- or ionic-size level at a selected temperature and pressure. The solvent should be capable of dissolving at least 0.1 mg of the polymer in 1 ml of the solvent, and more narrowly 0.5 mg in 1 ml at the selected temperature and pressure, for example, ambient temperature and ambient pressure.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples.

Example 1

Preparation of a Bioceramic Composite with Hydroxyapatite (HA) and Calcium Sulfate (CS) Nanoparticles Dispersed in a PLLA/(CL-co-GA)-b-PLLA Blend Step 1: Nano bioceramic HA/CS mixture is prepared by mixing 20 wt % HA and 80 wt % CS nano particles.

Step 2: The blend of PLLA, modifier copolymer, and HA/CS mixture with ratio of 100:10:4 is prepared by mixing 100 portions of PLLA, 10 portions of copolymer and 4 portions of HA/CS mixture through solution blending or mechanical blending. The blend is extruded to form tubing and then the tubing is cut into a stent after radial expansion. The expected degradation time of this blend stent is about 2 months shorter than that of PLLA/copolymer composite stent.

Example 2

Preparation of a Bioceramic Composite with Hydroxyapatite (HA) and Calcium Sulfate (CS) Nanoparticles Dispersed in a PLLA/(CL-co-GA)-b-PLLA Blend Step 1: Nano bioceramic HA/CS mixture is prepared by mixing 80 wt % HA and 20 wt % CS nano particles.

Step 2: The blend of PLLA, modifier copolymer, and HA/CS mixture with ratio of 100:10:4 is prepared by mixing 100 portions of PLLA, 10 portions of copolymer and 4 portions of HA/CS mixture through solution blending or mechanical blending. The blend is extruded to form tubing and then the tubing is cut into a stent after radial expansion. The expected degradation time of this blend stent is about 2 months longer than that of PLLA/copolymer composite stent.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising structural elements fabricated at least in part from a bioceramic/polymer composite, the composite having a plurality of bioceramic particles dispersed within a biodegradable polymer, the plurality of bioceramic particles comprising a first type including particles that do not have basic or acidic degradation by-products or hydrophilic surface groups and a second type including acidic or hydrophilic particles that increase the degradation rate of the polymer, and wherein the second type includes fluorine mica particles.

2. The stent according to claim 1, wherein the first type includes montmorillonite particles.

3. The stent according to claim 1, wherein the second type includes calcium sulfate particles.

4. The stent according to claim 1, wherein the plurality of bioceramic particles are nanoparticles.

5. The stent according to claim 1, wherein the bioceramic particles comprise montmorillonite particles and calcium sulfate particles.

6. The stent according to claim 1, wherein the polymer comprises poly(L-lactide) (PLLA) or poly(L-lactide-co-glycolide) (LPLG).

7. A stent comprising structural elements fabricated from a bioceramic/polymer composite, the composite having a plurality of bioceramic particles dispersed within a biodegradable polymer, the plurality of bioceramic particles comprising a first type including particles that do not have basic or acidic degradation by-products or hydrophilic surface groups and a second type including acidic or hydrophilic particles that increase the degradation rate of the polymer, wherein some or all of the second type of particles are encapsulated by a bioabsorbable polymer, wherein the first type of bioceramic particles are not encapsulated, wherein the first type of particles include fluorine mica particles, and wherein degradation of the encapsulated particles is reduced or prevented during a selected time frame by the bioabsorbable polymer encapsulating the particles.

8. The stent according to claim 7, wherein the encapsulating polymer is capable of reducing or preventing acceleration of the degradation of the composite polymer over the selected time frame due to the encapsulated particles.

9. The stent according to claim 7, wherein the encapsulating polymer is capable of reducing or preventing release of degradation by-products from the encapsulated particles during the selected time frame.

10. The stent according to claim 7, wherein the selected time frame is from a time of implantation of the stent until support by the stent of a lumen is no longer desired.

11. The stent according to claim 7, wherein the encapsulating polymer comprises a surface eroding polymer.

12. The stent according to claim 7, wherein the encapsulating polymer comprises a bulk eroding polymer.

13. The stent according to claim 7, wherein the second type includes calcium sulfate particles.

14. The stent according to claim 7, wherein the first type includes montmorillonite particles.

15. The stent according to claim 7, wherein the composite polymer comprises poly(L-lactide) (PLLA) or poly(L-lactide-co-glycolide) (LPLG).

* * * * *